US005939312A

United States Patent [19]

Baier et al.

[11] Patent Number: 5,939,312

[45] Date of Patent: Aug. 17, 1999

[54] MINIATURIZED MULTI-CHAMBER THERMOCYCLER

[75] Inventors: Volker Baier, Jena; Ulrich Bodner, Adelebsen; Ulrich Dillner, Jena; Johann Michael Köhler, Golmsdorf; Siegfried Poser, Jena; Dieter Schimkat, Göttingen, all of Germany

[73] Assignees: Biometra biomedizinische Analytik GmbH, Göttingen; Institut für Physikalische Hochtechnologie e.V, Jena, both of Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,649

[22] PCT Filed: May 17, 1996

[86] PCT No.: PCT/EP96/02111

§ 371 Date: Dec. 26, 1996

§ 102(e) Date: Dec. 26, 1996

[87] PCT Pub. No.: WO96/37303

PCT Pub. Date: Nov. 28, 1996

[30] Foreign Application Priority Data

May 24, 1995 [DE] Germany ........................... 195 19 015

[51] Int. Cl.[6] ............................. C12M 1/00; C12P 19/34; G01N 21/00

[52] U.S. Cl. ........................ 435/287.2; 435/91.1; 422/50; 422/63

[58] Field of Search ......................... 435/6, 287.2, 287.3, 435/287.9, 288.4, 91.1, 91.2, 183; 422/50, 63, 68.1, 82.12, 99; 536/23.1, 24.33; 935/85

[56] References Cited

U.S. PATENT DOCUMENTS

| | | | |
|---|---|---|---|
| 5,229,580 | 7/1993 | Chioniere | 219/521 |
| 5,475,610 | 12/1995 | Atwood et al. | 364/500 |
| 5,585,069 | 12/1996 | Zanzucchi et al. | 422/100 |
| 5,602,756 | 2/1997 | Atwood et al. | 364/500 |
| 5,616,301 | 4/1997 | Moser et al. | 422/104 |
| 5,646,039 | 7/1997 | Northrup et al. | 435/287.2 |

FOREIGN PATENT DOCUMENTS

| | | |
|---|---|---|
| 0092140A1 | 10/1983 | European Pat. Off. . |
| 0545736A2 | 6/1993 | European Pat. Off. . |
| 4435107C1 | 4/1996 | Germany . |
| WO9322058 | 11/1993 | WIPO . |
| WO9405414 | 3/1994 | WIPO . |

OTHER PUBLICATIONS

*Clinical Chemistry*, vol. 40, No. 9, Sep. 1, 1994, pp. 1815–1818, XP000444699 Wilding P et al.: "PRC in a Silicon Microstructure" see p. 1815, right–hand column, paragraph 4 –p. 1817, right–hand column, paragraph 1.

"Molekulare Zellbiologie", Walter de Gruyter, Berlin–New York 1994, pp. 256–257 by Darnell, J.; Lodish, H.; Baltimore, D.

A. Rolfs et al., "PCR: Clinical Diagnostics and Research", p. 29–31, Springer Laboratory, Berlin/Heidelberg, 1992.

C.C. Oste et al. "The Polymerase Chain Reaction", Birkhäuser, Boston/Basel/Berlin (1993), p. 165.

Marktübersicht Gentechnologie III, Nachr. Chem. Tech. Lab. 41, 1993, M2, M4, M5 and M6.

Northrup et al. "DNA Amplification With A Microfabricated Reaction Chamber", The 7th International Conference on Solid State Sensors and Actuators, Proc. Transducers 1993, pp. 924–926.

*Primary Examiner*—Bradley L. Sisson
*Attorney, Agent, or Firm*—Jordan and Hamburg LLP

[57] ABSTRACT

A miniaturized multi-chamber thermocycler provides a thermocycler which is easy to handle, and permits the treatment of a great number of samples of small sample volumes at high temperature changing rates and at low heating powers. A sample receptacle body manufactured in micro-system technics provides a plurality of sample chambers which are embodied such that at least one of the sample chamber walls of the sample chamber which constitutes the sample chamber base is an efficient heat conductor and also of low mass. Said sample chambers are coupled to a coupling body, serving as heat sink, established via at least one poor heat conducting bridge which, with respect to its dimensioning and/or material selection is such that its specific heat conductance λ is smaller 5 W/K°·m. The sample chambers are provided with at least one heating element which is constructed to effect, in connection with a sample chamber wall serving as heat balancing layer which simultaneously can be the sample chamber base, a substantially homogeneous temperature distribution in a fluid insertable into the sample chambers.

34 Claims, 3 Drawing Sheets

MINIATURIZED MULTI-CHAMBER THERMOCYCLER

BACKGROUND OF THE INVENTION

The present invention relates to a miniaturized multi-chamber thermocycler particularly applicable in polymerase chain reaction methods in which desired DNA sequences are amplified, as well as for carrying out other thermally controlled biochemical and biological molecular processes.

Thermally controlled biochemical and biological molecular processes very often involve procedural steps conducted at different temperatures. Such exposure to varying temperatures is particularly applicable to the polymerase chain reaction.

The polymerase chain reaction (PCR) has been recently developed to amplify definite DNA sequences, and its essential features have been outlined, for example, in "Molekulare Zellbiologie", Walter de Gruyter, Berlin-New York 1994, pg. 256/257' by Darnell, J.; Lodish, H.; Baltimore, D. As noted, PCR requires thermal cycling of mixtures of DNA sequences. To this end, stationary sample treatment devices containing reaction chambers are employed into which the respective samples are introduced and then subjected to periodical heating and cooling, the respectively desired DNA sequences being amplified in accordance with the specifically preselected primers contained in the samples.

Presently, PCR is preferably carried out on a plurality of samples in one-way plastic vessels (microtubes) or in standardized micro-titre plates. The sample volumes used therein range between about 10 and 100 $\mu$l (A. Rolfs et al, Clinical Diagnostics and Research, Springer Laboratory, Berlin/Heidelberg, 1992). Recently, C. C. Oste et al., The Polymerase Chain Reaction, Birkhäuser, Boston/Basel/Berlin (1993), page 165, reports the use of smaller sample volumes ranging from about 1 to 5 $\mu$l.

The above referred microtubes are subjected to a temperature regime of conventional heating and cooling units (Marktübersicht Gentechnologie III, Nachr. Chem. Tech. Lab. 41, 1993, M1). Due to the bulky nature of such typical heating and cooling units, parasitic heat capacities of transmitter, and heating and cooling elements physically limit a reduction in the cycle times, in particular with reduced sample volumes. As much as 20 to 30 seconds is required for the temperature of the samples in the microtubes to reach desired equilibrium. Moreover, in practice, overheating and subcooling cannot be entirely avoided. In addition, one of the greatest problems with a PCR carried out in microtubes is that the temperature gradients within the samples may lead to differences in temperatures up to 10° K. To overcome this drawback, heatable covers have been employed with some effectiveness, however resulting in increased cost of the apparatus.

For purposes of automation of PCR, micro-titre plates predominantly made of heat-proof polycarbonate are used for charging and sample analysis. These behave thermally in a manner similar to the microtubes mentioned hereinbefore, however, they are more advantageous when used in manual or automatic sample charging. Overall, the devices used for these applications are bulky and not easy handle.

The effectiveness of the prior sample chambers is subject to a variety of drawbacks. Therefore, a miniaturized sample chamber has recently been proposed (Northrup et al, DNA Amplification with microfabricated reaction chamber, 7th International Conference on Solid State Sensors and Actuators, Proc. Transducers 1993, pg. 924–26) which permits a four times faster amplification of desired DNA-sequences than prior known arrangements. The sample chamber, taking up to 50 $\mu$l sample liquid, is made of a structurized silicon cell with a longitudinal extension in an order of size of 10 mm which, in one sample injection direction, is sealed by a thin diaphragm via which the respective temperature exposure is executed by miniaturized heating elements. Also, with this device, the DNA sequence to be amplified is inserted via micro-channels into the cell, subjected to a polymerase chain reaction and subsequently drawn off. Notwithstanding the advantages obtained with said device, the reaction chamber has to be heated and cooled in its entity, resulting in only limited rates of temperature changes. Particularly with a further reduction in the sample sizes, the parasitic heat capacity of the reaction chamber, and, if employed, of a tempering block, becomes more dominant to the reaction liquid, so that the high temperature changing rates otherwise feasible with small liquid volumes cannot be achieved. This feature renders the efficiency of said method comparatively low. Additionally, a comparatively expensive control system is required to obtain a respective constant temperature regime for the reaction liquid, since the heating and cooling power applied to the samples, is substantially consumed in the ambient structure units rather than in the reaction liquid. The essential disadvantage, however, of the last mentioned device lies in the fact that it does not permit an extension for simultaneous and parallel treatment of a plurality of samples.

SUMMARY OF THE INVENTION

Accordingly, it is an object of the present invention to provide a miniaturized multichamber thermocycler which, though easy to handle, permits treatment of a plurality of samples having volumes in the lower micro- and nano-liter range.

It is a further object to provide a miniaturized multichamber thermocycler which permits a high temperature changing speed and requires low heating power, wherein individual samples are subject to a comparatively homogeneous temperature distribution and wherein overheating and subcooling effects are substantially eliminated.

According to these and other objects of the invention, there is provided a sample receptacle body manufactured in accordance with micro-system techniques, and which comprises a plurality of sample chambers and which provides a defined coupling to a heat sink via at least one poor heat conducting bridge.

DETAILED DESCRIPTION OF THE INVENTION

Figure 1:
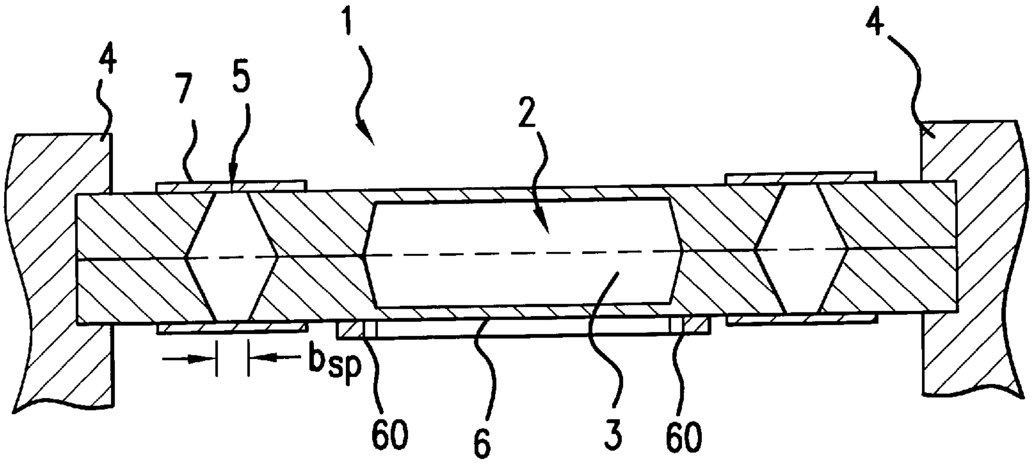
FIG. 1 is a lateral section of a part of a first embodiment of the invention.

Referring to FIG. 1, a miniaturized multi-chamber thermocycler is schematically represented in a lateral section, comprising a sample receptacle mount 1 which has to be a rather good heat conductor. In the example depicted, a silicon wafer is conveniently used as sample receptacle mount 1 in which, by a suitable conventional process of deep-etching, a plurality of properly configured sample chambers 2 are provided such that a sample chamber base 3 thus formed simultaneously provides low mass structure and sufficient heat conductivity. The deep-etching is performed in the region to the right and to the left of sample chamber 2 until only thin strips 5 remain. The width of said strips is designated $b_{sp}$ which is, within the scope of the invention, an essential parameter variably adaptable to the other sample receptacle mount 1 parameters. In the example of FIG. 1, strips 5 are provided with a bridge 7 of poor heat conductivity for which thin glass plates, $SiO_2$ or $Si_3N_4$ plates are suited. In addition, coatings made of such materials and deposited in a suitable manner, such as for example varnish, may be used, or corresponding combinations of the aforementioned materials. In the depicted example, pyrex glass plates of about 200 μm thickness are used for bridge 7. The parameters used in the selection and dimensioning are, apart from the strip width $b_{sp}$ which is, for example, 40 μm, the specific heat conductance $\lambda_{ü}$ of the bridge and its thickness dü, wherein according to the invention values between about 0.6 and 6 W/K·m have to be maintained for one relation of the modified heat conductance value $G'=(\lambda_{ü}\cdot d_{ü})/b_{sp}$.

In the example disclosed, sample receptacle mount 1 is advantageously formed by assembling two identical partial mounts, manufactured as described hereinabove with regard to sample chamber base 3, in mirror symmetry about an axis designated by dash-lines. It is noted that this is a technologically advantageous embodiment to which the invention is not to be restricted. Other designs of a sample chamber covering are also feasible, for example, those comprised of foils of suitable heat conductivity. The sample chamber base 3 is provided with a heating element 6, 60 which is advantageously a thin-layer heating element attached to the bottom side of the sample chamber base to permit facilitated integration into the manufacturing process. It is also within the intended scope of the invention to provide the sample chamber cover with respective arrangements of heating elements symmetric with sample chamber base 3. Sample chamber base 3 operates as a heat compensation layer, hence, the samples (not shown) insertable into sample chamber 2 are subject to a homogeneous temperature gradient during both heating cycles as well as cooling cycles. The arrangement described is laterally framed by coupling bodies 4, only partially shown, which serve as heat sinks.

Figure 2:
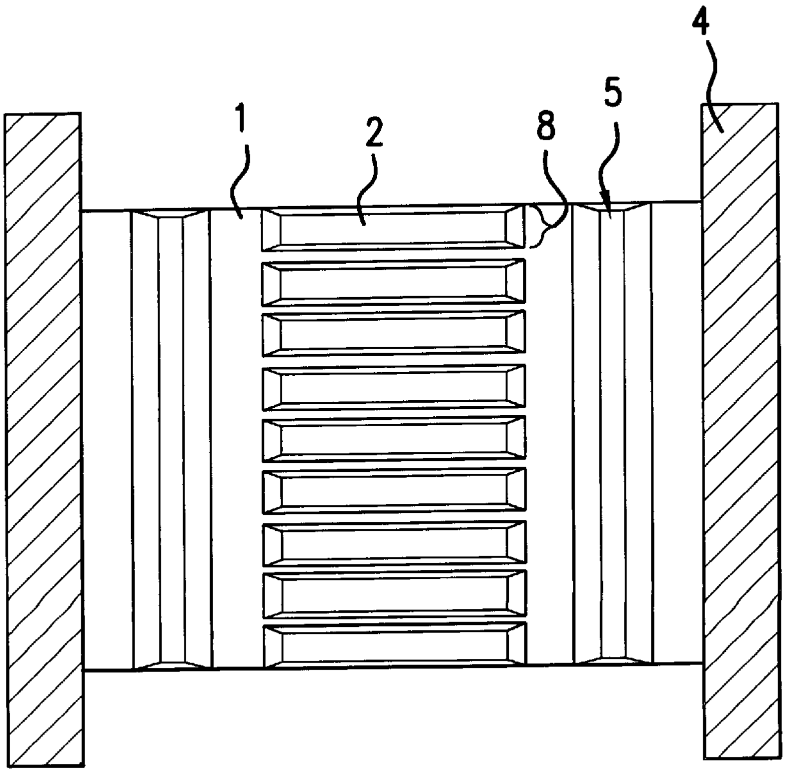
FIG. 2 is a plan view of an open sample receptacle mount embodied according to FIG. 1.

In FIG. 2, the arrangement according to FIG. 1 is illustrated schematically and not-to-scale, with the sample chamber cover removed. In practice, at least 96 sample chambers 2 are arranged along silicon wafer receptacle mount 1, the respective narrow sides 8 of which are followed by strips 5 on both sides. The volume of the respective individual sample chambers 2 amounts to, for example, about 2 to 10 μl, depending on the particular application. The thickness of sample chamber base 3, which as mentioned operates like a heat compensation layer, can be dimensioned, for example, about 100 μm. Only very low values between about 0.5 and 5 W are required for the heating power per sample chamber 2. By virtue of the invention, time constants between about 1 and 6 seconds, and cooling rates between about 5 and 25 K°/s at required temperature steps of about 80° K can be realized in carrying out the abovementioned PCR process. The temperature difference within a sample liquid is below 5° K, thus virtually eliminating sample overheating and subcooling.

Figure 3:
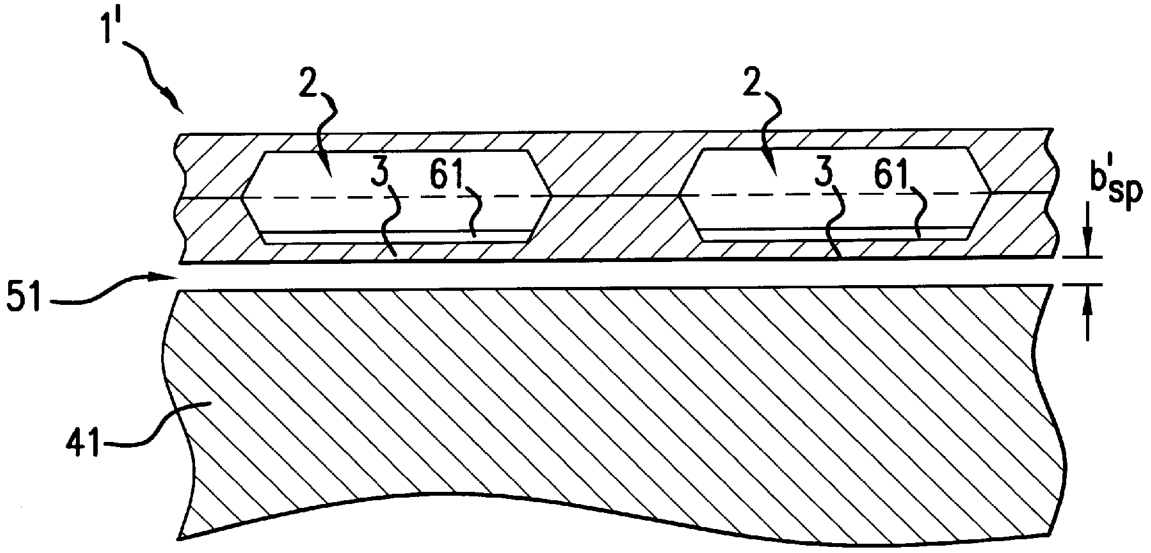
FIG. 3 is a part of a lateral sectional view of a second embodiment of the invention.
Figure 4:
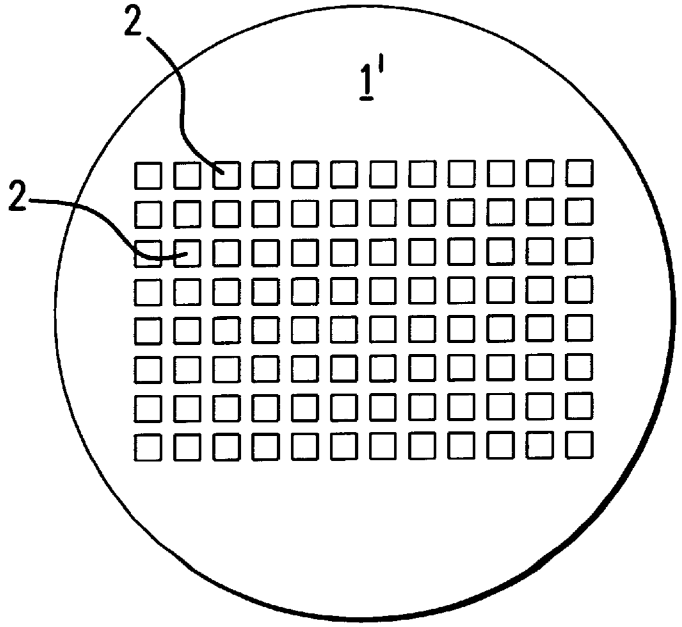
FIG. 4 is a plan view of an alternative embodiment of a sample receptacle mount according to FIG. 3.

Turning now to FIG. 3, a part of a lateral section of a second advantageous embodiment of the invention is depicted. The manufacture of sample receptacle mount 1' is assumed to correspond to that described with respect to the embodiment FIG. 1. In contrast to the first embodiment, however, sample chambers 2 are arranged in a suitable array along a silicon wafer which is technologically still more advantageous and, moreover, permits a higher number of sample chambers per wafer. In practice, such an embodiment permits accommodation of about 6000 sample chambers, each providing about 0.1 μl volume capacity, in one 4"-silicon wafer. The invention is not restricted to the rectangular plan views of the individual sample chambers 2 as schematically shown in FIG. 4. Circular geometries are also feasible when the etching process is respectively carried out.

In the present embodiment, the poor heat conducting bridge in accordance with the invention is provided by a slit 51 between the sample chamber base 3 and the coupling body 41 operating as heat sink. Such bridge embodiment considerably increases the degree of freedom when the desired dimension of slit 51 defined as $b'_{sp}$ is selected. Hence, the slit width $b'_{sp}$ may be varied in steps by employing precisely pre-manufactured spacers of different height and, alternatively slit width $b'_{sp}$ may be variably set by means of more expensive adjustment mechanisms. These alternatives are particularly advantageous when gases or liquids are used as materials for the poor heat conducting bridges. Moreover, it is feasible with said embodiment to provide totally covering intermediate layers or coatings in the slit space. However, in this regard it is an essential that slit 51 is constituted with respect to the material and/or to the thickness in a manner that a value between about 300 and 3000 W/K·m$^2$ is satisfied at a relation $\lambda_{sp}/b'_{sp}$, where $\lambda_{sp}$ is the specific heat conductance in the slit.

Figure 5:
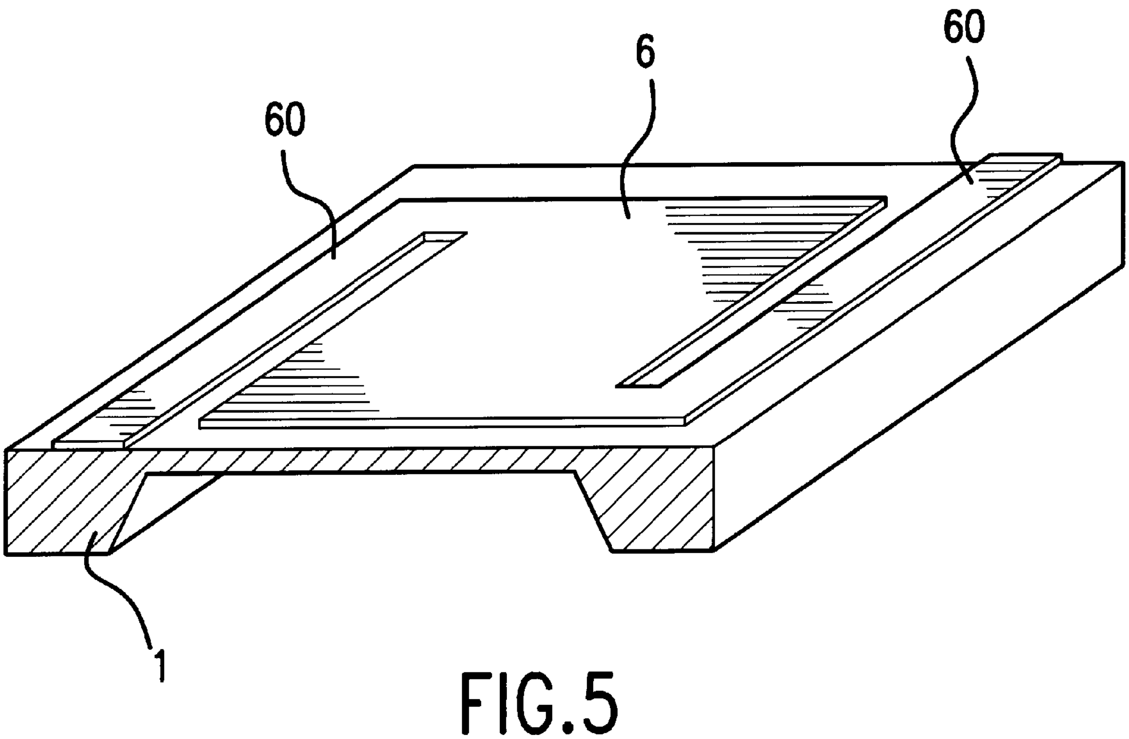
FIG. 5 is one embodiment of a heating element in accordance with the invention.

Finally, FIG. 5 represents a section of a suitably configured heating element as might be employed in accordance with the invention, in plan view of the sample chamber base 3 (or the cover of corresponding configuration) according to FIG. 1. A resistance heating layer, initially covering the entire area, is formed in such a manner that, adjacent and below sample base 3, a broader heating element range and smaller heating strips 60 result at the rim portions of the respective sample chamber on top of the solid ranges of the sample receptacle mount 1. Thus, greater heating power input into each of the sample chambers 2 is ensured in said ranges.

The specifications concerning structuring, as described hereinbefore, are analogously valid for FIG. 3 wherein the employed heating elements 61 are represented, for the sake of simplicity, as being positioned within the sample chambers. Particularly when the sample chamber cover is also provided with respective heating elements, the structuring of the heating elements is such that a greater heating power input into sample chambers 2 is achieved on that side of sample receptacle mount 1' which is adjacent coupling body 41. For ease of manufacture, the heating elements of this example, just as in FIG. 1, are attached to the bottom side of the sample receptacle mount 1' and on top of the cover, respectively, when executed in practice.

The low heat capacity of the proposed entire system achieves heating and cooling rates which, with reduced expenditures for apparatus, are far superior to those of conventional thermocyclers. With a first prototype, and water as a test medium, temperature changing rates of 15 K°/s were obtained without any problem. During the heating and cooling phase the temperature differences within a sample only are in an order of size of 5 K. After setting of the thermal balance, the former nearly drops to 0 K. The thermal balance within a sample is achieved in a time period in an order of size of about 10 s.

By virtue of the invention, active temperature control in connection with a low thermal relaxation time of the sample receptacle body, the temperature changing rates are adaptable as desired between about 1 and 15 K/s to the respective conditions of a given PCR experiment.

The features disclosed in the specification, in the subsequent claims, and in the drawings are, individually as well as in any combination, considered as being essential for the invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

We claim:

1. A miniaturized multi-chamber thermocycler, comprising:

a sample receptacle mount for receiving fluids, said sample receptacle mount including sample chambers formed therein for receiving said fluids;

each of said sample chambers being bounded by sample chamber walls including a sample chamber base whereat heat is applied to and removed from said sample chambers, and sampler chamber side walls;

a coupling support body supporting said sample receptacle mount and functioning as a heat sink;

said sample receptacle mount including means for coupling said sample chambers to said coupling support body;

said means for coupling including at least one bridge coupling said sample chambers to said coupling support body and said at least one bridge having a specific heat conductance λ less than 5 W/K·m to limit heat transfer between said sample chambers and said coupling support body; and said sample chamber base including at least one heating element with said sample chamber base functioning as a heat balancing layer.

2. The miniaturized multi-chamber thermocycler as claimed in claim 1, wherein:

said sample chambers are rectangular with said sample chamber bases being elongated and said side walls include end side walls, opposing one another, which are narrower than an elongate direction of said sample chamber bases;

said sample chambers are arranged in a row with said elongate direction of said sample chamber base being transverse to said row and said end side walls being disposed at opposing sides of said row; and said at least one bridge includes a strip member, formed by etching said sample receptacle mount, extending parallel to said row and adjacent at least one of said end side walls of each of said sample chambers to connect said sample chambers to said coupling support body.

3. The miniaturized multi-chamber thermocycler as claimed in claim 2, further including an insulating bridge member disposed on said strip member and on portions of said sample receptacle mount bordering sides of said strip member.

4. The miniaturized multi-chamber thermocycler as claimed in claim 3, wherein a material of said insulating bridge member is selected from a group of materials consisting of a glass plate, a coating of $SiO_2$, a coating of $Si_3N_4$, and coating of a varnish.

5. The miniaturized multi-chamber thermocycler as claimed in claim 2, wherein said at least one heating element is a microstructurized thin layer heater connected to said sample chamber base and having a configuration which provides greater heat at portions of said sample chambers proximate said at least one of said end side walls than at remaining portions of said sample chambers.

6. The miniaturized multi-chamber thermocycler as claimed in claim 3, wherein a material of said sample receptacle mount is silicon.

7. The miniaturized multi-chamber thermocycler as claimed in claim 6, wherein a material of said insulating bridge member is selected from a group of materials consisting of a glass plate, a coating of $SiO_2$, a coating of $Si_3N_4$, and coating of a varnish.

8. The miniaturized multi-chamber thermocycler as claimed in claim 6, wherein said sample chambers have a volume in a range of 2 μl to 10 μl.

9. The miniaturized multi-chamber thermocycler as claimed in claim 1, wherein a material of said sample receptacle mount is silicon.

10. The miniaturized multi-chamber thermocycler as claimed in claim 9, wherein said sample chambers have a volume in a range of 2 μl to 10 μl.

11. The miniaturized multi-chamber thermocycler as claimed in claim 9, wherein said sample chambers have a volume in a range of 2 μl to 10 μl.

12. A miniaturized multi-chamber thermocycler, comprising:

a sample receptacle mount for receiving fluids, said sample receptacle mount including sample chambers formed therein for receiving said fluids;

each of said sample chambers being bounded by sample chamber walls including a sample chamber base, whereat heat is applied to and removed from said sample chambers, and sampler chamber side walls;

a coupling support body supporting said sample receptacle mount;

said sample receptacle mount including means for coupling said sample chambers to said coupling support body;

said means for coupling including at least one bridge coupling said sample chambers to said coupling support body;

said sample chamber base including at least one heating element and said sample chamber base functioning as a heat balancing layer;

said sample chambers being rectangular with said sample chamber bases being elongated and said side walls including end side walls, opposing one another, which are narrower than an elongate direction of said sample chamber bases;

said sample chambers being arranged in a row with said elongate direction of said sample chamber bases being transverse to said row and said end side walls being disposed at opposing sides of said row;

said at least one bridge including a strip member, formed by etching said sample receptacle mount, extending parallel to said row and adjacent at least one of said end side walls of each of said sample chambers to connect said sample chambers to said coupling support body;

said at least one bridge including an insulating bridge member disposed on said strip member and on portions of said sample receptacle mount bordering sides of said strip member; and said at least one bridge satisfying a relation $G'=(\lambda_{ü}d_{ü})/b_{sp}$, where G' is a modified heat conductance having a value between 0.6 and 6 W/K°·m, $\lambda_{ü}$ is a specific heat conductance of said at least one bridge and is smaller than 5 W/K·m, $d_{ü}$ is a thickness of said at least one bridge, and $b_{sp}$ is a width of said strip member extending in a direction of a thermal gradient between said sample chambers and said coupling support body.

13. The miniaturized multi-chamber thermocycler as claimed in claim 12, wherein a material of said sample receptacle mount is silicon.

14. The miniaturized multi-chamber thermocycler as claimed in claim 13, wherein said sample chambers have a volume in a range of 2 $\mu$l to 10 $\mu$l.

15. The miniaturized multi-chamber thermocycler as claimed in claim 12, wherein said sample chambers have a volume in a range of 2 $\mu$l to 10 $\mu$l.

16. A miniaturized multi-chamber thermocycler, comprising:

a sample receptacle mount for receiving fluids, said sample receptacle mount including sample chambers formed therein for receiving said fluids;

each of said sample chambers being bounded by sample chamber walls including a sample chamber base and sampler chamber side walls;

a coupling support body supporting said sample receptacle mount and functioning as a heat sink;

said sample receptacle mount including means for coupling said sample chambers to said coupling support body;

said means for coupling including at least one bridge having a specific heat conductance $\lambda$ less than 5 W/K·m;

said sample chambers having at least one heating element;

said sample receptacle mount having a bottom surface spaced from the coupling support body to define a gap;

said sample chamber bases forming portions of said bottom surface and being arranged in a common plane; and said at least one bridge includes a bridge substance filling said gap between said bottom surface and said coupling support body to connect the sample chambers to the coupling support body.

17. The miniaturized multi-chamber thermocycler as claimed in claim 16, wherein a relationship $\lambda_{sp}/b'_{sp}$ has a value between 300 and 3000 W/K·m$^2$, where $\lambda_{sp}$ is a specific heat conductance within said gap and $b'_{sp}$ is a width of said gap.

18. The miniaturized multi-chamber thermocycler as claimed in claim 17, wherein said bridge substance includes at least one material selected from a group consisting of a $SiO_2$-plate, a $Si_3N_4$-plate and a glass plate.

19. The miniaturized multi-chamber thermocycler as claimed in claim 17, wherein said bridge substance includes one of a fluid and a gaseous medium.

20. The miniaturized multi-chamber thermocycler as claimed in claim 16, wherein said sample bases include said at least one heating element such that said sample chamber bases function as heat balancing layers.

21. The miniaturized multi-chamber thermocycler as claimed in claim 16, wherein a material of said sample receptacle mount is silicon.

22. The miniaturized multi-chamber thermocycler as claimed in claim 21, wherein said sample chambers have a volume in a range of 2 $\mu$l to 10 $\mu$l.

23. The miniaturized multi-chamber thermocycler as claimed in claim 16, wherein said sample chambers have a volume in a range of2 $\mu$l to 10 $\mu$l.

24. A miniaturized multi-chamber thermocycler, comprising:

a sample receptacle mount for receiving fluids, said sample receptacle mount including sample chambers formed therein for receiving said fluids;

each of said sample chambers being bounded by sample chamber walls including a sample chamber base, whereat heat is applied to and removed from said sample chambers, and sampler chamber side walls;

a coupling support body supporting said sample receptacle mount;

said sample receptacle mount including at least one bridge coupling said sample chambers to said coupling support body;

said sample chamber base including at least one heating element and said sample chamber base functioning as a heat balancing layer;

said sample chambers being rectangular with said sample chamber bases being elongated and said side walls including end side walls, opposing one another, which are narrower than an elongate direction of said sample chamber bases;

said sample chambers being arranged in a row with said elongate direction of said sample chamber bases being transverse to said row and said end side walls being disposed at opposing sides of said row;

said at least one bridge including a strip member, formed by etching said sample receptacle mount, extending parallel to said row and adjacent at least one of said end side walls of each of said sample chambers to connect said sample chambers to said coupling support body;

said at least one bridge including an insulating bridge member disposed on said strip member and on portions of said sample receptacle mount bordering sides of said strip member; and said at least one bridge satisfying a relation $G'=(\lambda_{ü}d_{ü})/b_{sp}$, where G' is a a modified heat conductance having a value between 0.6 and 6 W/K°·m, $\lambda_{ü}$ is specific heat conductance of said at least one bridge and is smaller than 5 W/K·m, $d_{ü}$ is a thickness of said at least one bridge, and $b_{sp}$ is a width of said strip member extending in a direction of a thermal gradient between said sample chambers and said coupling support body.

25. The miniaturized multi-chamber thermocycler as claimed in claim 24, wherein said sample chambers have a volume in a range of 2 $\mu$l to 10 $\mu$l.

26. A miniaturized multi-chamber thermocycler, comprising:

a sample receptacle mount for receiving fluids, said sample receptacle mount including sample chambers formed therein for receiving said fluids;

each of said sample chambers being bounded by sample chamber walls including a sample chamber base and sampler chamber side walls;

a coupling support body supporting said sample receptacle mount and functioning as a heat sink; said sample receptacle mount including at least one bridge having a specific heat conductance $\lambda$ less than 5 W/K·m;

said sample chambers having at least one heating element;

said sample receptacle mount having a bottom surface spaced from the coupling support body to define a gap;

said sample chamber bases forming portions of said bottom surface and being arranged in a common plane; and said at least one bridge includes a bridge substance filling said gap between said bottom surface and said coupling support body to connect the sample chambers to the coupling support body.

27. The miniaturized multi-chamber thermocycler as claimed in claim 26, wherein said sample chambers have a volume in a range of 2 μl to 10 μl.

28. A miniaturized multi-chamber thermocycler, comprising:

a sample receptacle mount for receiving fluids, said sample receptacle mount including sample chambers formed therein for receiving said fluids;

each of said sample chambers being bounded by sample chamber walls including a sample chamber base whereat heat is applied to and removed from said sample chambers, and sampler chamber side walls;

a coupling support body supporting said sample receptacle mount and functioning as a heat sink;

said sample receptacle mount including at least one bridge coupling said sample chambers to said coupling support body and said at least one bridge having a specific heat conductance A less than 5 W/K·m to limit heat transfer between said sample chambers and said coupling support body; and said sample chamber base including at least one heating element with said sample chamber base functioning as a heat balancing layer.

29. The miniaturized multi-chamber thermocycler as claimed in claim 28, wherein said sample chambers have a volume in a range of 2 μl to 10 μl.

30. A miniaturized multi-chamber thermocycler, comprising:

a sample receptacle mount for receiving fluids, said sample receptacle mount including sample chambers formed therein for receiving said fluids;

each of said sample chambers being bounded by sample chamber walls including a sample chamber base, whereat heat is applied to and removed from said sample chambers, and sampler chamber side walls;

a coupling support body supporting said sample receptacle mount;

said sample receptacle mount including at least one bridge coupling said sample chambers to said coupling support body so as to thermally insulate said sample chambers from said coupling support body;

said sample chamber base including at least one heating element and said sample chamber base functioning as a heat balancing layer; and said at least one bridge being a strip member formed in said receptacle mount such that said strip member has a thickness less than a thickness of a remainder of said sample receptacle mount surrounding said sample chambers and connects said sample chambers to said coupling support body so as to thermally insulate said sample chambers from said coupling support body.

31. The miniaturized multi-chamber thermocycler as claimed in claim 30, wherein said at least one bridge satisfies a relation $G'=(\lambda_{ü} d_{ü})/b_{sp}$, where G' is a a modified heat conductance having a value between 0.6 and 6 W/K°·m, $\lambda_{ü}$ is specific heat conductance of said at least one bridge and is smaller than 5 W/K·m, $d_{ü}$ is a thickness of said at least one bridge, and $b_{sp}$ is a width of said strip member extending in a direction of a thermal gradient between said sample chambers and said coupling support body.

32. The miniaturized multi-chamber thermocycler as claimed in claim 31, wherein said sample chambers have a volume in a range of 2 μl to 10 μl.

33. The miniaturized multi-chamber thermocycler as claimed in claim 30, wherein said at least one bridge has a specific heat conductance λ less than 5 W/K·m.

34. The miniaturized multi-chamber thermocycler as claimed in claim 33, wherein said sample chambers have a volume in a range of 2 μl to 10 μl.

* * * * *